United States Patent
Gover et al.

(10) Patent No.: US 9,494,551 B2
(45) Date of Patent: Nov. 15, 2016

(54) MULTI-FUNCTIONAL SENSOR FOR AN ELECTROCHEMICAL DETECTION SYSTEM

(71) Applicant: VANTIX HOLDINGS LIMITED, Jersey (GB)

(72) Inventors: Andy Gover, Cambridgeshire (GB); Kathleen Vincent, Cambridgeshire (GB); Julianne Dillon, Cambridgeshire (GB); Bryan Perrotti, Cambridgeshire (GB); Christopher J. Morse, Cambridgeshire (GB); Douglas Vincent, Cambridgeshire (GB); Kristin Jugenheimer Size, Cambridgeshire (GB)

(73) Assignee: Vantix Holdings Limited, St. Heiler (JE)

( * ) Notice: Subject to any disclaimer, the term of this patent is extended or adjusted under 35 U.S.C. 154(b) by 0 days.

(21) Appl. No.: 14/759,922

(22) PCT Filed: Jan. 30, 2014

(86) PCT No.: PCT/GB2014/050255
§ 371 (c)(1),
(2) Date: Jul. 8, 2015

(87) PCT Pub. No.: WO2014/118549
PCT Pub. Date: Aug. 7, 2014

(65) Prior Publication Data
US 2015/0346143 A1 Dec. 3, 2015

Related U.S. Application Data

(60) Provisional application No. 61/758,567, filed on Jan. 30, 2013.

(51) Int. Cl.
*G01N 27/416* (2006.01)
*B01L 3/00* (2006.01)

(52) U.S. Cl.
CPC ......... *G01N 27/4163* (2013.01); *B01L 3/5027* (2013.01); *B01L 2200/0684* (2013.01); *B01L 2200/143* (2013.01); *B01L 2300/0645* (2013.01); *B01L 2300/0825* (2013.01)

(58) Field of Classification Search
CPC ............ G01N 27/4163; B01L 3/5027; B01L 2200/142; B01L 2200/0684; B01L 2300/0645; B01L 2300/0825
See application file for complete search history.

(56) References Cited

U.S. PATENT DOCUMENTS

2005/0054078 A1* 3/2005 Miller ............... B01L 3/502707
435/287.1
2011/0253224 A1* 10/2011 Linder ................. B01L 3/5027
137/2

* cited by examiner

*Primary Examiner* — J. Christopher Ball
(74) *Attorney, Agent, or Firm* — Polsinelli PC

(57) ABSTRACT

Provided herein is a system, including a platform for performing at least one assay protocol. The platform may include a flow cell that can include at least one sensor. The platform may also include a reader that can be in communication with the sensor. Moreover, the sensor may maintain communication with the reader for the entirety of the performance of the assay protocols to transmit data regarding physical events within the flow cell or an electrochemical state of any substance contained within the flow cell.

9 Claims, 8 Drawing Sheets

MULTI-FUNCTIONAL SENSOR FOR AN ELECTROCHEMICAL DETECTION SYSTEM

CROSS-REFERENCE

The present disclosure claims priority to U.S. Provisional Application Ser. No. 61/758,567 filed Jan. 30, 2013, and entitled "Multi-Functional Sensor for An Electrochemical Detection System," which is incorporated herein by reference in its entirety.

FIELD

The present invention generally relates to an electrochemical detection system for conducting electrochemical analysis, and more particularly to an electrochemical detection system that includes one or more sensors active throughout the performance of one or more assay protocols to receive nearly constant real time quality control feedback regarding the performance of the assay protocols.

BACKGROUND

Electrochemistry is a branch of chemistry that studies chemical reactions occurring in a solution at the interface of an electron conductor and an electrolyte. The reaction can involve electron transfer between the electron conductor and the electrolyte. For example, the electron conductor may be an electrode comprising a metal or a semiconductor.

Under some circumstances, the chemical reactions discussed above may be driven by applying either an externally derived voltage or a voltage created by the chemical reaction. Under these circumstances, these chemical reactions are known as electrochemical reactions. Moreover, some chemical reactions where electrons are transferred between one or more molecules are known as oxidation/reduction or redox reactions. Generally, electrochemistry relates to situations where oxidation and reduction reactions are separated in space or time and are connected by an external electric circuit that may be used to understand the reaction.

Some electrochemical analyses can be undertaken in a disposable cartridge that may include a reagent for inducing electrochemical reactions monitored, detected, or quantified by one or more sensors. Some conventional cartridges may be configured to operatively engage a reader device that initiates a protocol, such as via the mechanical actuation of the cartridge. Furthermore, the reader device may receive data signals that may be processed to produce test results of the reaction occurring within the cartridge.

Many conventional systems with or without cartridges use passive systems for quality control and quality assurance. For example, some systems rely on the reader device to monitor the functions within the system and quality control checks during the performance of the assays. Moreover, in some conventional systems, these checks are performed only at the beginning and the end of the performance of the assay, with little to no monitoring during the assay itself. As a result, some conventional assays are not properly monitored and stringent quality control cannot be maintained during the performance of the assays.

Moreover, at least some conventional systems do not include sensors that can monitor physical events during the performance of the assays. For example, some conventional sensors are not configured to detect physical events occurring within the system, such as fluid fronts, to enable a user and the system to monitor the progress of the assay and to ensure that the components are properly functioning and calibrated.

SUMMARY

Embodiments of the electrochemical detection system include a platform for performing at least one assay protocol. The platform includes a flow cell with at least one sensor. Moreover, the sensor may be in communication with a reader that can at least partially control the performance of the assay protocols. During the entire performance of the assay protocols, for example from the initiation until completion of the assay, the sensor detects physical events within the flow cell and an electrochemical state of an analyte contained within the flow cell. In particular, during the entire performance of the assay protocols, the sensor transmits data to the reader regarding the physical events or the electrochemical state of the substance within the flow cell. For example, the sensor is configured to detect the presence or absence of fluid within the flow cell or the presence of one or more air bubbles within the flow cell. In one aspect, the sensor can also transmit information regarding the physical events or the electrochemical state to the reader, thereby enabling the reader to record changes within the flow cell for quality assurance or quality control.

In one aspect, the platform also includes an air source in selective fluid flow communication with the flow cell. The air source is configured to provide a volume of air to the flow cell to wash the sensor during the performance of the assay protocols. For example, in one embodiment, the only wash agent to be used with the platform may be a volume air, to the exclusion of other wash agents.

The electrochemical detection system includes a cartridge and a reader. The cartridge includes at least one activatable container. In one aspect, at least one container includes a volume of air to be used as a wash agent. The cartridge may also include at least one fluid channel that can be in selective fluid flow communication with at least one flow cell for performing at least one assay protocol. Moreover, at least one sensor may be operatively associated with each flow cell for detecting a reaction during the performance of the assay protocols. The sensors detect physical events or an electrochemical state within the flow cells. In addition, the sensors may be configured to detect the presence or absence of fluid within the flow cell, or the presence of one or more air bubbles within the flow cell.

Moreover, the reader may be adapted to be operatively engaged to the cartridge for initiating the performance of the assay protocols. In some aspects, the sensors transmit information regarding the physical events and electrochemical state to the reader. In addition, the reader can control the performance of the assays at least partially based upon the information regarding the physical events and electrochemical state. In one aspect, the reader includes at least one mechanical actuator that engages at least one container The electrochemical detection system includes a method for performing an assay. The method includes providing at least one sensor at least partially disposed within a flow cell. Moreover, the method also includes providing a reader in communication with the sensor. In one aspect, the method includes using the sensor to detect one or more physical events within the flow cell and an electrochemical state of any substance in substantial contact with the sensor. The sensor continuously transmits information regarding the electrochemical state and physical events of the flow cell to the reader during the entirety of the performance of the assay. Moreover, the sensor is also configured to detect the presence or absence of fluid within the flow cell or the presence of one or more air bubbles within the flow cell.

The method also includes introducing a sample into the flow cell so that the sample contacts at least a portion of the sensor and introducing a volume of air into the flow cell. For example, the volume of air may be used to wash the flow cell and the sensor, and to remove the sample from the flow cell. In addition, the reader may be configured to control the performance of the assay at least partially based on the information received from the sensor regarding the electrochemical state and physical events of the flow cell.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
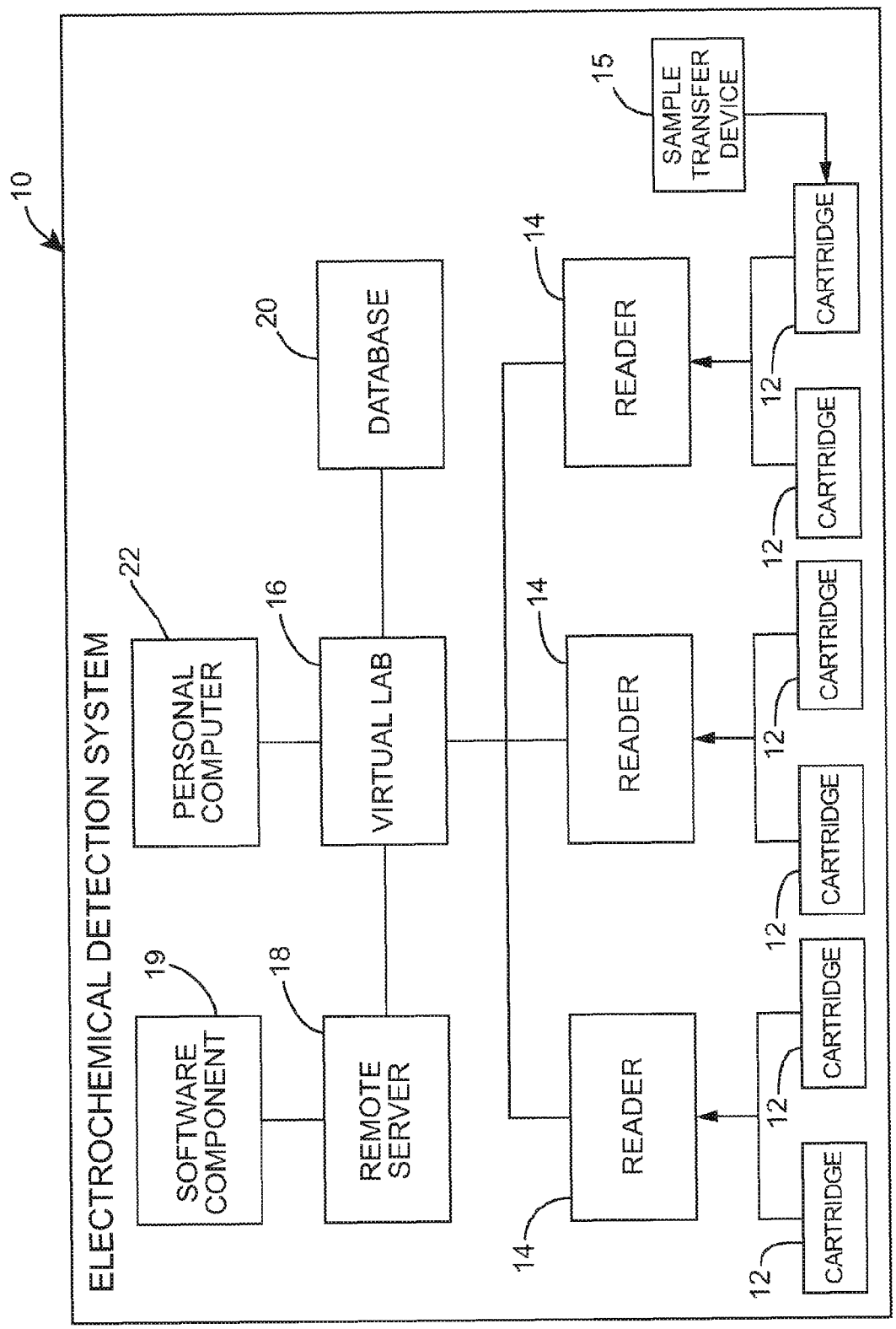
FIG. 1 is simplified block diagram illustrating the different components of the electrochemical detection system.

Referring to the drawings, an embodiment of the electrochemical detection system is illustrated and generally indicated as 10 in FIG. 1. The electrochemical detection system 10 provides a means for conducting at least one assay protocol on a single disposable cartridge 12 when operatively engaged to a reader 14. Optionally, the cartridge 12 is operatively engaged to a sample transfer device 15. In addition, the electrochemical detection system 10 may include at least one reader 14 in operative communication with a virtual lab 16 for communicating data, such as test results or calibration information, between the readers 14 and a remote server 18 associated with the virtual lab 16. The virtual lab 16 retrieves information from a database 20 using a personal computer 22. As described in greater detail below, some embodiments of the electrochemical detection system 10 may include one or more sensors 28. In some embodiments, the sensors 28 may be active during a final phase of the at least one assay protocol to aid in reading or otherwise assessing the results of the assays.

In some embodiments, the sensors 28 may be active throughout the performance of the at least one assay protocol to assess and/or monitor any changes, for example physical, electrical, chemical changes, and the like, within a local environment of the sensors 28. As a result, substantially or completely real-time data may be gathered during the performance of the at least one assay protocol to monitor quality control criteria to ensure accurate and sensitive results.

Figure 2:
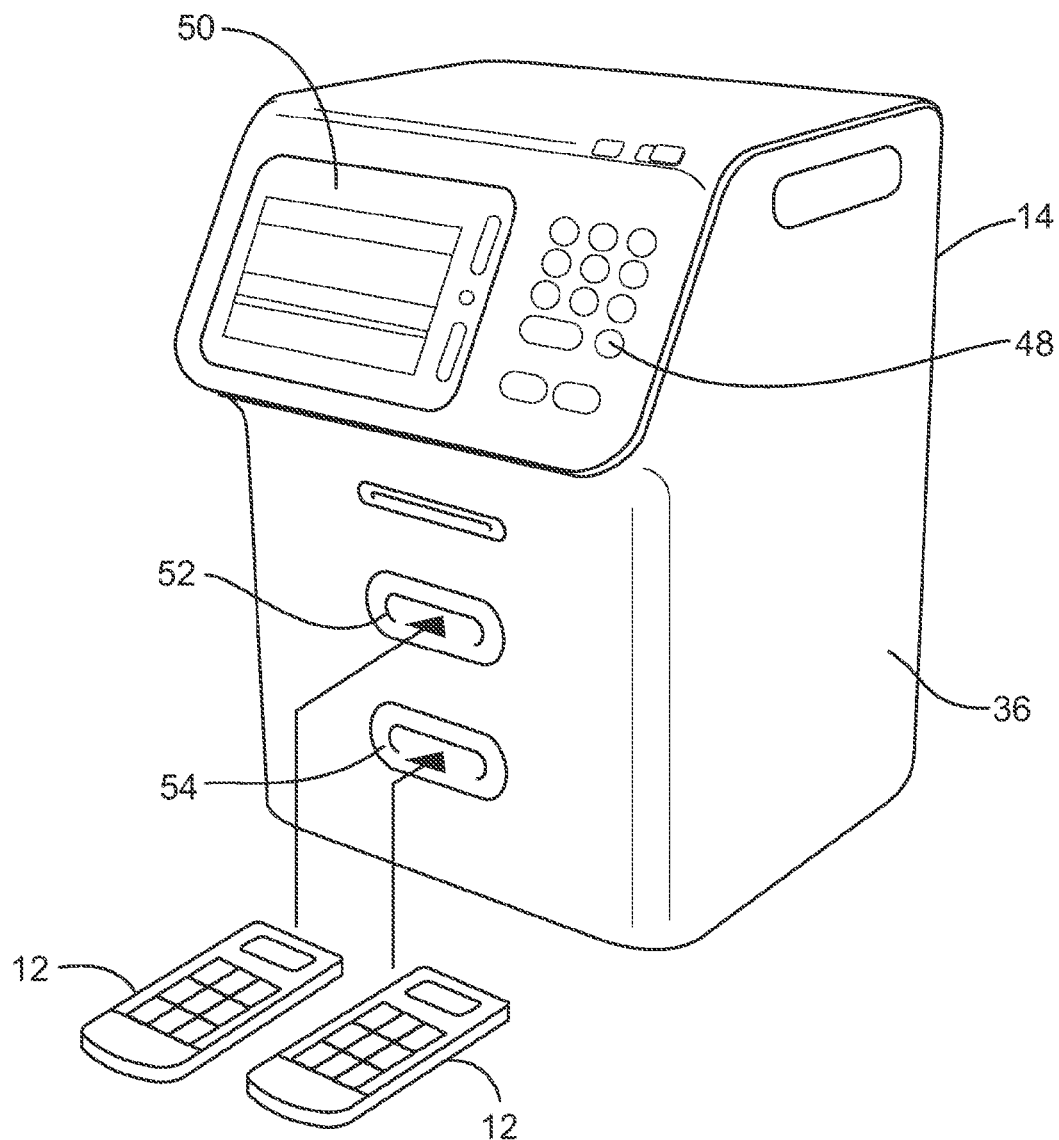
FIG. 2 is a simplified illustration showing the cartridge and reader arrangement.

As shown in FIG. 2, each reader 14 may include a reader body 36 having a control panel 48 that permits the user to perform at least one assay protocol when a respective cartridge 12 is operatively engaged to the reader 14. In one embodiment, the reader 14 may include a first docking station 52 and a second docking station 54 for operative engagement of a respective cartridge 12 with the reader 14, although other embodiments of the reader 14 may include one or more docking stations for engaging any number of respective cartridges 12. The reader 14 may further include a screen 50 that acts as a user interface and a communication component (not shown) that permits the reader 14 to operatively communicate with the virtual lab 16 through the remote server 18.

Figure 3:
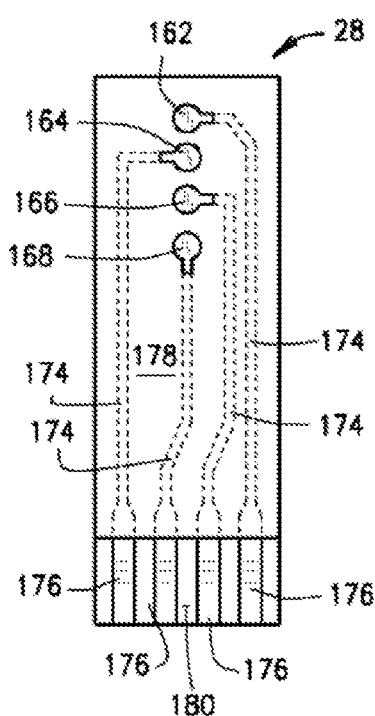
FIG. 3 is a top view of the sensor arrangement used in the cartridge for electrochemical detection.
Figure 4:
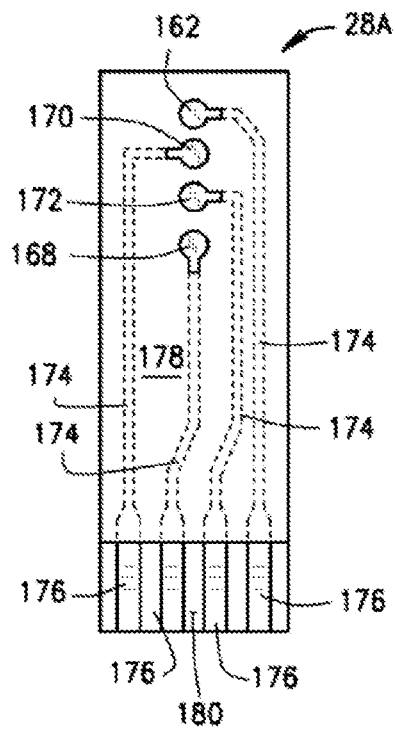
FIG. 4 is a top view of another embodiment of the sensor arrangement used in the cartridge for electrochemical detection.
Figure 5:
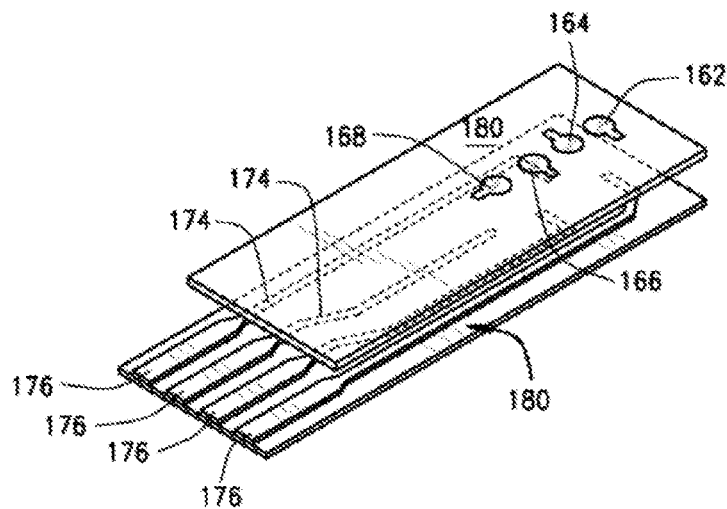
FIG. 5 is an exploded view of the sensor arrangement shown in FIG. 3.
Figure 6:
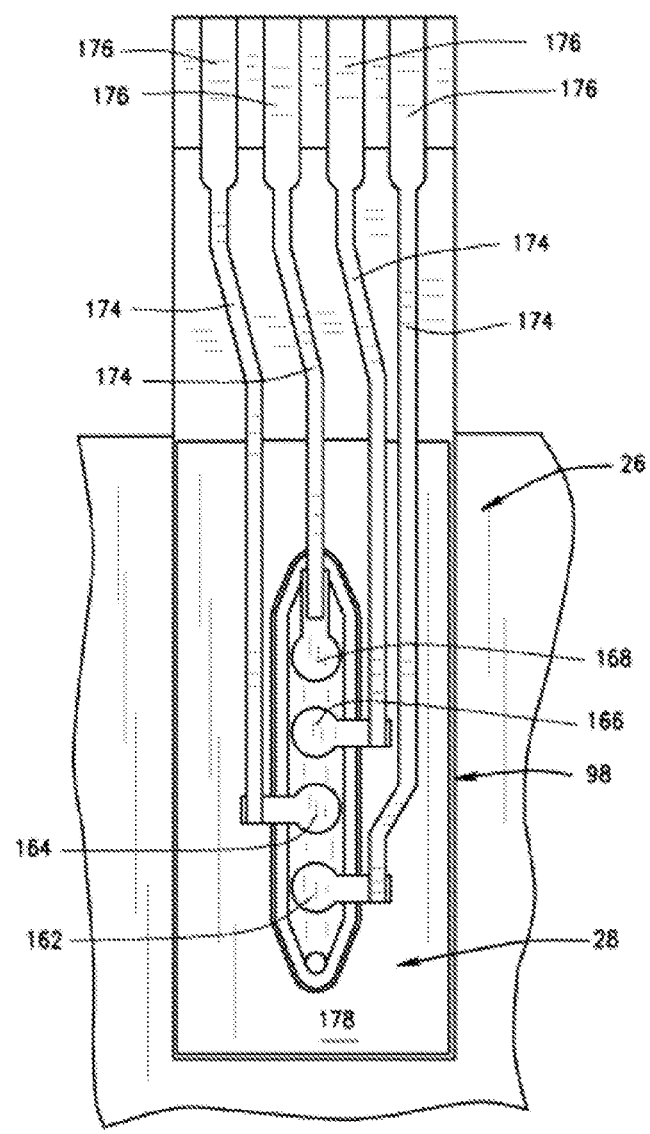
FIG. 6 is a plan view of the sensor operatively engaged to the flow cell.

Referring to FIGS. 3, 4, and 6, a sensor 28 may be operatively engaged to a flow cell to detect the reactions created by performance of an assay protocol. In one embodiment, the sensor 28 may have a four-electrode arrangement that consists of a working electrode 162, first and second working calibration electrodes 164 and 166, and a reference electrode 168. The electrodes 162, 164, 166 and 168 are engaged to conductive portions 174 conductively connected to a respective contact 176 for operative engagement with the reader 14 for providing the signals from detected by sensor 28 to the software component 19 for processing of data.

In one aspect, the sensors 28 may be constructed using a three-step process. In the first step, four layers are screen-printed onto a flexible sheet of insulating plastic backing 180. The first layer comprises electrically conductive silver tracks followed by a second layer of a silver/silver chloride (Ag/AgCl) reference electrode 168. A third layer consisting of a carbon working electrode is screen-printed over a portion of each conductive silver track, and then a fourth layer of a dielectric insulating layer 178 is applied over the areas of the plastic backing 180 other than those areas of the plastic backing 180 containing working electrodes 162, 164, and 166. The dielectric layer 178 also covers the conductive portions 174, for example silver or other conductive material, to inhibit liquids from coming into contact with the conductive portions 174 during the immersion in solutions or during the performance of a particular assay protocol. The resulting printed sheet contains at least one sensor 28 in which rows of sensors 28 are cut from the printed sheet for the second step of the process. Sensors in this format may be used for process control, such as bubble detection and flow measurement. For use as the main diagnostic component, the second and third steps of the manufacture process also are used.

The second step involves a polymerization wherein the screen-printed sensors 28 are secured in a lid (not shown) of an electrochemical cell. Each row of sensors 28 has an exposed electrically conductive bar across the top of the row of sensors 28 to which each conductive portion 174 of the working electrodes 162, 164, and 166 are electrically connected. When the rows of sensors 28 are secured in the cell lid, an electrical connection between the cell and the conductive portions 174 is established. The bottom half of the cell contains a series of wells (not shown) to hold the polymerization solution and also the counter-electrodes for the electrochemical polymerization. The polymerization solution, for example, may contain a pyrrole monomer and a counterion.

A polymerization solution is placed into the wells of the electrochemical cell and the lid (with the row of sensors 28) is placed onto the cell. The working electrodes 162, 164, and 166 may be immersed in the polymerization solution. A computer-controlled galvanostat may be used to apply a series of current steps that drives current between the working electrodes 162, 164, and 166 of the sensor 28 (anode) and the counter-electrode in the cell (cathode). The resulting polypyrrole conductive film forms on the working electrodes 162, 164, and 166 of each sensor 28. Once the polymerization occurs, the rows of sensors 28 are removed from the lid of the cell and soaked in a high purity water, for example Milli-Q, to remove residual counter-ions or unreacted monomer. After soaking, the rows of sensors 28 are placed in an incubator and allowed to dry for a predetermined time, for example 17 hours or overnight.

In the third step, the rows of polymerized sensors 28 may be placed onto racks that control the orientation of the rows. The rack filled with rows of sensors 28 may be placed onto the table of a bio-reagent dispensing system (not shown). The bio-reagent dispensing system dispenses the appropriate bio-reagents for the assay onto the polymerized working electrodes 162, 164, and 166 of each sensor 28. After the sensors 28 on a rack have been coated with the bio-reagent, the rack is removed from the bio-reagent dispensing system and placed in an incubator (not shown) to dry. For some bio-reagents, after drying the rows of sensors 28 are immersed in a stabilizer coating solution to preserve the activity of the bio-reagents. When the bio-reagents and any additional coatings are dry, the rows of sensors 28 are cut into the final shape of sensor 28 for use. During this step, the conductive bar used during the polymerization is removed and the electrical contacts 174 on the sensor 28 are trimmed flush to allow correct engagement with the reader 14 when the cartridge 12 is inserted into either docking station 52 or 54.

In the alternative, as shown in FIG. 4, the sensor 28A may include three working electrodes 162, 170, and 172 and a reference electrode 168 which are associated with a respective conductive portion 174 and have a similar configuration as the embodiment of sensor 28. The working electrodes 162, 170 and 172 may be averaged by the software component 19 to reduce the coefficient of variance from each electrode 162, 170 and 172.

In one aspect, the electrochemical detection system 10 includes the capability of performing rapid immunoassay reactions within cartridge 12 by the sequentially controlled release of fluids through the flow cell chambers 94A, 96A, and 98A when the assay protocols are conducted. Based on reaction kinetics and thermodynamics, higher concentrations of these molecules in the same vicinity result in faster reaction rates.

Some embodiments of the electrochemical detection system 10 may operate in a generally similar manner to some previously mentioned embodiments, but with different physical configurations. In some embodiments, in lieu of the previously mentioned cartridge 12, the electrochemical detection system 10 may operate using a general platform, including a support structure. For example, the support structure may function in a substantially similar manner to the fluidics backbone 26. The support structure does not require the same configurations as discussed above. Accordingly, no embodiment discussed herein must use a fluidics backbone 26 of the configuration discussed above. Rather, some embodiments of the electrochemical detection system 10 may include a support structure with other configurations to support one or more flow cells that may each comprise at least one sensor. Furthermore, in some embodiments, the support structure may be used in lieu of the fluidics backbone 26 and bonded the blister pack 24 in a manner substantially similar to the one described above.

For example, in some embodiments, the electrochemical detection system 10 may include a general platform, such as in lieu of or in addition to a cartridge 12, for performing one or more electrochemical assays. The platform may include a support structure that may function in a similar manner to the fluidics backbone 26 and may include at least one channel in selective fluid flow communication with one or more flow cells. In some embodiments, the at least one channel and the one or more flow cells may be similar, for example similar in configuration or function to the channels 88, 90, and 92 and flow cells 94, 96, and 98 discussed above. Moreover, at least one sensor may be disposed within the one or more flow cells and the at least one sensor may comprise a similar function or configuration to the sensors 28 and electrodes 162, 164, 166, and 168 discussed above. In addition, the sensors may be disposed in other apparatuses, such as a fermentor or a cell culture reactor.

Moreover, the sensors may be configured and arranged to detect, measure, or otherwise assess an electrochemical state of a substance, such as an analyte, reagent, conjugate, and the like, in a local environment, for example the flow cell. In some embodiments, the sensors may also be configured to detect one or more physical events or conditions within the local environment. For example, the sensors may be configured to detect the presence or absence of a fluid within the local environment (e.g., fluid fronts), the presence of gas within the local environment (e.g., air bubbles), ionic concentration, relative pressure changes, solution format, contaminants, solute concentration, mechanical, or electronic switching events, and many other potentially relevant events or conditions within the local environment of the sensor.

In some embodiments, the sensors may transmit this information to a reader (e g., similar to the reader 14) or another component that can control the performance of at least one assay. The sensors may transmit the information related to the electrochemical state and physical events or conditions to the reader. As a result, the reader may process this information for substantially or completely real-time quality control or quality assurance of the assays being performed, as well as for use in controlling the performance of the assays, for example in a real-time feedback loop.

For example, the data transmitted by the sensors to the reader may be used by the reader to assess the current physical state of the local environment of the sensors to ensure that the assay is proceeding within acceptable limits and that fluids passing over the sensor do so within an acceptable timeframe. In particular, because the sensor can detect pressure and fluid flow or fluid fronts, the data sent to the reader may be used to control and manage fluid flow, for example through feedback. As a result, the fluid flow may be accurately controlled via the reader using the real-time data provided by the sensors. For example, by being able to control the fluid flow during the assay, the need for precision pumps and precision fluidics may be at least partially mitigated relative to embodiments without this configuration. Moreover, the data may also indicate the presence of an air bubble or other abnormal event immediately adjacent to the sensors, which may indicate that data obtained from that sensor during the assay is unreliable. Overall, the data sent to the reader may be used as both a quality control mechanism and an avenue for asserting control over fluid flow within the system.

In some embodiments, to accomplish the quality control or fluid control during the performance of the assays, the sensors may be actively monitored for at least a portion of the performance of the assays. In some embodiments, the sensors may be active or monitored for the entirety of the performance of the assays. For example, the performance of the assay may begin by activating the sensors such that the sensors immediately or nearly immediately begin transmitting data regarding the electrochemical state, physical events, or conditions of the local environment to the reader. The sensors may then remain active during the assay and the final or nearly final step in the assay may be deactivating or ceasing to monitor the sensors. As a result, data regarding the electrochemical state, physical events, or conditions near the sensor may be transmitted to the reader throughout the assay so that the reader can ensure quality control or quality assurance of the assay, in addition to controlling the performance of the assay.

In some embodiments, the general platform for performing electrochemical assays may be configured and arranged to enable washing of one or more flow cells using one or more fluids. Specifically, as previously mentioned, components of the electrochemical detection system 10 may be washed at each step of the protocol to ensure acceptable levels of precision and sensitivity.

Generally, and by way of example only, the electrochemical detection system 10 may employ three fluidic processing steps with at least two intermediate washing steps to ensure adequate washing between the fluidic processing steps. In particular, the fluidic processing steps may include circulating a sample, reagent, or conjugate through the at least one channel and into the flow cells. Then, the sample, reagent, or conjugate may be washed from the flow cells by circulating a wash reagent one or more times through the flow cells and over the sensors to remove any undesirable substances, such as excess sample, reagent, or conjugate. Moreover, this process may be repeated multiple times until the assays are complete.

In some embodiments, the fluid used to wash the flow cells may be a liquid, such as water, an aqueous solution, for example phosphate buffered saline (PBS); an alcohol, for example ethanol or methanol; acetonitrile, dimethylformamide (DMF), dimethylsulfoxide (DMSO), or other polar solvent. In other embodiments, the fluid may be air or a similar gas, such as nitrogen, argon, helium, or oxygen. Specifically, in some embodiments, the fluid may only be air to the exclusion of other washing fluids or substances. In other words, in some embodiments, the only substance used to wash the flow cells or the sensors is a type of air or other gas.

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements. The terms comprising plurality do not exclude the method where there is only "one of".

EXAMPLES

The following examples detail some manners in which one skilled in the art can employ some embodiments of the electrochemical detection system 10. The following examples are not intended to be limiting of the disclosure and the claims, but rather an illustrative discussion regarding some uses of the system.

Example 1

Assay Protocol—TSH—Typical Sandwich Immunoassay

The conjugate is first diluted at a ratio of 1:500 in thyroid stimulating hormone (TSH) conjugate buffer and the calibrant is diluted in a TSH sample diluent to provide a concentration of 100, 10, 1, 0.1, and 0.01 mIU/mL. Sample was added using a volume of 150 µL and a flow rate of 1 µL per second. The assay protocol may add 150 µL of conjugate at a flow rate of 1 µL per second followed by 400 µL of wash buffer at a flow rate of 3 µL per second. Finally, 200 µL of substrate was added at a flow rate of 3 µL per second. For example, phosphate buffered saline (PBS) may be used as the wash buffer, while SigmaFAST may be used as the substrate in a concentration of one set of SigmaFAST tablets for every 50 mL MilliQ water. The following flow times may be used: TSH sample at 2.5 minutes, conjugate at 2.5 minutes, wash buffer at 2.25 minutes, substrate at 1.25 minutes, and read time at 1 minute and 40 seconds. As such, the assay protocol may be performed in less than 10 minutes.

The sensors 28 are read using an applied voltage of −115 mV for 10 seconds and allowing an open circuit potential (OCP) for 90 seconds. The mV reading at the end of the 90-second OCP was taken as the final value.

Example 2

Detection of Events

Figure 7A:
FIGS. 7A-7C are images of use of an embodiment of an electrochemical detection system.
Figure 7B:
Figure 7C:

Using the electrochemical detection system 10 shown in FIGS. 7A-7C, a TSH assay protocol was performed using a substantially similar method as detailed above at Example 1. In brief, a series of three sensors were used to measure the TSH present in a blood specimen. Initially, a blood sample was introduced into the flow cell and incubated with the sensors. The sensors were washed using a volume of air. Next a volume of conjugate flowed over the three sensors, after which another volume of air was used to wash the sensors. Finally, a reading solution (substrate) was passed over the sensors.

Figure 8:
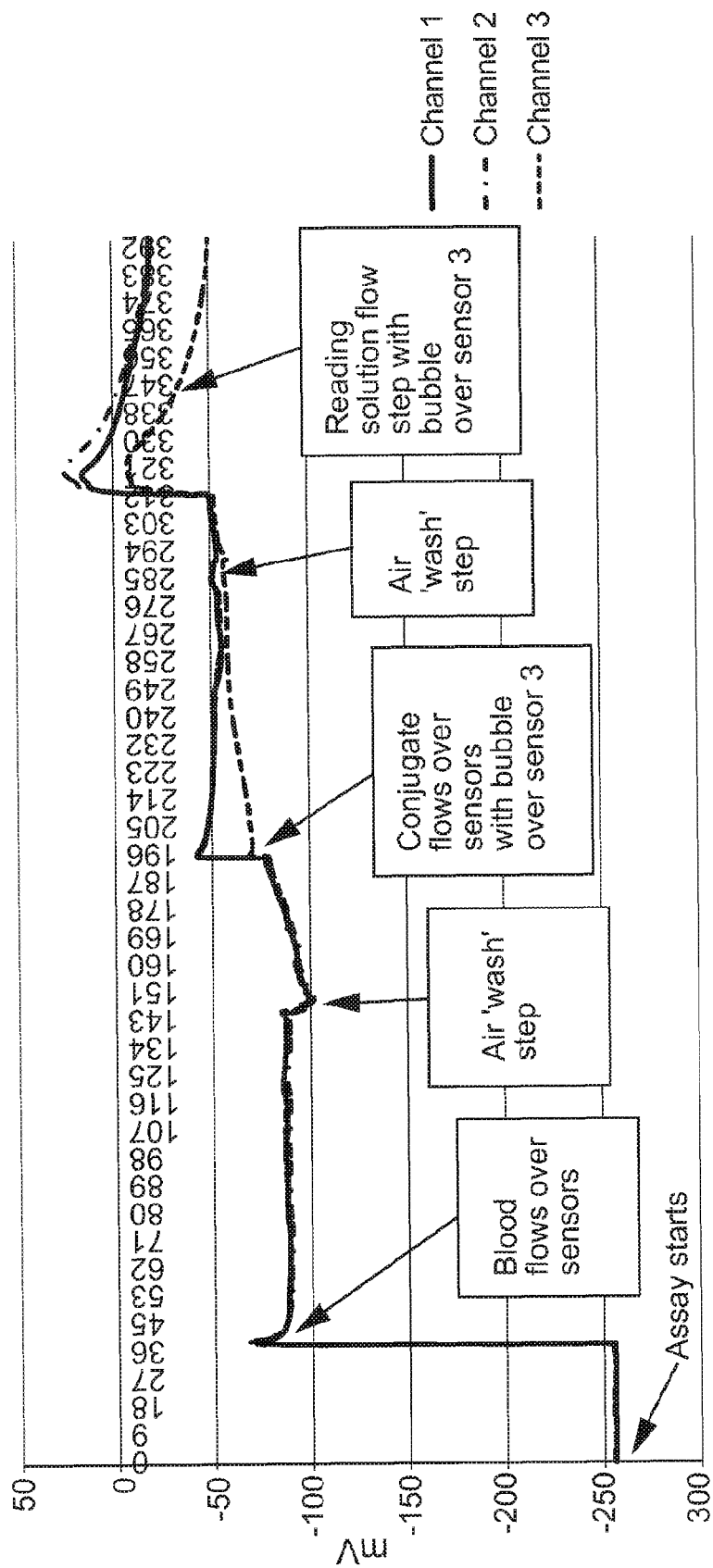
FIG. 8 is a line graph showing potential values in millivolts during the use shown in FIGS. 7A-7C.

During the performance of the TSH assay, the three sensors were active and measuring potential of the local environment surrounding each sensor. FIG. 8 shows the potential values in millivolts (mV) during the performance of the assay, starting at 0 seconds and ending at 392 seconds. The data of FIG. 8 show that constant monitoring of the sensors can reveal information about the assay that would not be readily available if the sensors were only active when the reading solution was passed over the sensors. In particular, the data illustrate that after the first air wash, an air bubble became trapped over sensor 3 (the left-most sensor seen in FIGS. 7B and 7C). As a result, the potential values recorded from this sensor were skewed compared to the other two sensors. Although the air bubble did not block sensor 3 or affect the other two sensors, the air bubble prevented the accurate detection of the potential at sensor 3 during the performance of the TSH assay. In particular, the values recorded at sensor 3 did not show the increase in potential seen after adding the conjugate and the reading solution as detected by the other two sensors. The data from sensor 3 could be removed from the set so as to not skew averaging or later statistical processing.

Figure 9:
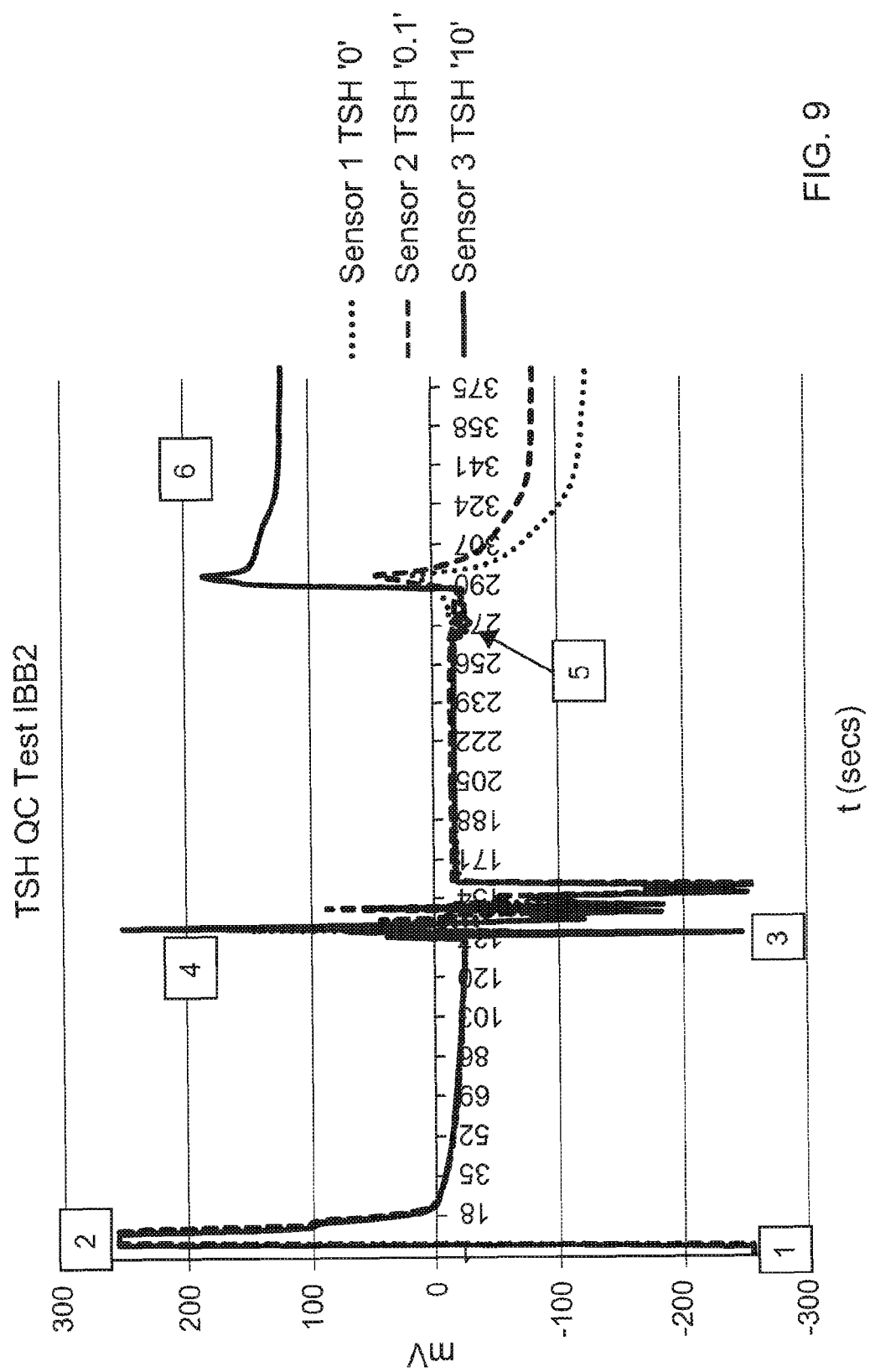
FIG. 9 is a line graph showing potential values in millivolts during the use of an embodiment of the electrochemical detection system.

Next, referring to FIG. 9, a similar TSH assay was performed and monitored from start to finish using the three sensors. The data in FIG. 9 illustrate the relationships between the steps of the assay and the potential detected by each sensor. The numbered events of FIG. 9 illustrate the changing local environment adjacent to the sensors and how this changing environment impacts the sensors, as seen in the recorded potential values. Specifically, point 1 corresponds to the initiation of the assay such that the potential value is not detected. Next, point 2 corresponds to a fluid front in which fluid (the sample) begins to pass over the sensors. The potential values associated with a series of bubbles are seen in point 3. These potential values fluctuate because of the presence of the air bubbles. Next, points 4 and 5 both correspond to additional fluid fronts (i.e., conjugate and substrate and reading solution, respectively) that reached the sensors. Finally, point 6 corresponds to the reading phase whereby the final potential values are measured for data generation related to TSH quantification. Similar to the data discussed above, the graph of FIG. 9 further illustrates the use of constant monitoring of the sensors during the performance of the assay.

Figure 10:
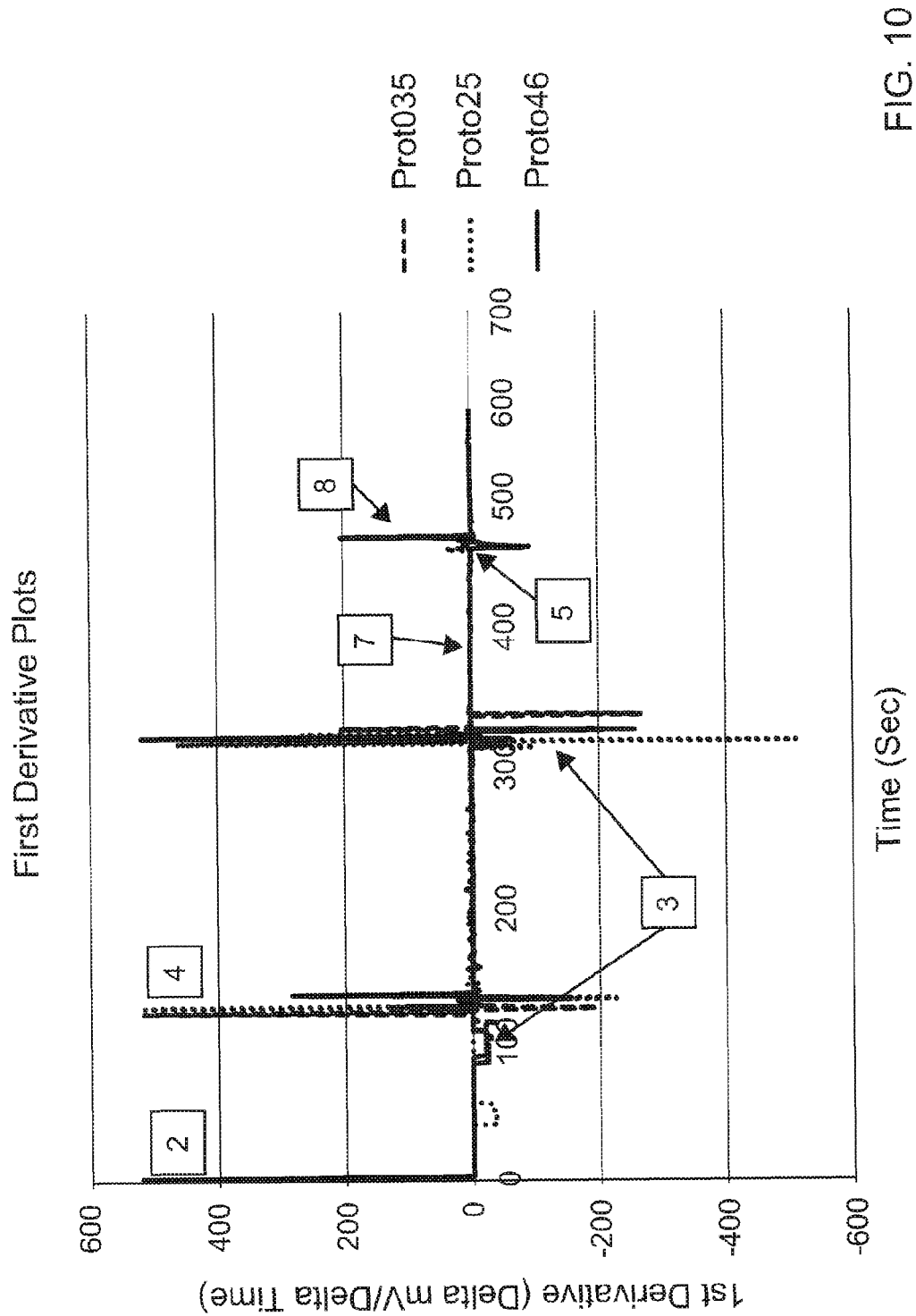
FIG. 10 is a plot of a first derivative of the data shown in FIG. 9.

Next, a first derivative of the data in FIG. 9 was plotted in the graph of FIG. 10, which can be used by the software of the reader to give exact exposure times; that is, the time that the sensor has been exposed to a particular fluid. These data can be used to significantly improve precision between different assay runs. The point numbers in FIG. 10 correspond to the same point numbers discussed above. There is no derivative data for point 1 because no signal was produced in the first place; the sensor was in contact with only air. In addition, point 7 illustrates a stable signal during the reaction, as the derivative is equal to about zero and point 8 corresponds to an initial kinetics electrochemical signal.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An electrochemical detection system comprising:
   a cartridge comprising at least one activatable container including a volume of air to be used as a flow cell wash agent, and at least one fluid channel in selective fluid flow communication with at least one flow cell for performing at least one assay protocol;
   at least one sensor operatively associated with the at least one flow cell for detecting a reaction during the performance of the at least one assay protocol, the at least one sensor being configured to detect a physical event within the at least one flow cell or an electrochemical state of an analyte located within the at least one flow cell during the performance of the at least one assay protocol; and
   a reader adapted to be operatively engaged to the cartridge for initiating performance of the at least one assay protocol;
   wherein the reader is configured to control the performance of the at least one assay protocol at least partially based upon the data regarding the physical event or the electrochemical state; and
   wherein the activatable container containing air is configured to provide a volume of air to the flow cell.

2. The electrochemical detection system of claim 1, wherein the physical event includes the presence or absence of a fluid within the at least one flow cell.

3. The electrochemical detection system of claim 1, wherein the at least one sensor is configured to detect the presence of one or more air bubbles within the at least one flow cell.

4. The electrochemical detection system of claim 1, comprising more than one activatable container.

5. A method for performing an assay, the method comprising:
   providing an electrochemical detection system comprising:
      a cartridge comprising at least one activatable container including a volume of air to be used as a flow cell wash agent, and at least one fluid channel in selective fluid flow communication with at least one flow cell for performing at least one assay protocol;
      at least one sensor operatively associated with the at least one flow cell for detecting a reaction during the performance of the at least one assay protocol, the at least one sensor being configured to detect a physical event within the at least one flow cell or an electrochemical state of an analyte located within the at least one flow cell during the performance of the at least one assay protocol;
      a reader adapted to be operatively engaged to the cartridge for initiating performance of the at least one assay protocol;
      wherein the reader is configured to control the performance of the at least one assay protocol at least partially based upon the data regarding the physical event or the electrochemical state; and
      wherein the activatable container containing air is configured to provide a volume of air to the flow cell;
   detecting with the at least one sensor the physical event within the flow cell or the electrochemical state of a substance in substantial contact with the at least one sensor;
   introducing a sample into the flow cell so that the sample contacts at least a portion of the at least one sensor; and
   introducing the volume of air from the activatable container into the flow cell to wash the flow cell and the at least one sensor, and to remove the sample from the flow cell;
   wherein the at least one sensor continuously transmits information regarding the physical event or the electrochemical state to the reader during the performance of the assay.

6. The method of claim 5, wherein the physical events include the presence or absence of a fluid within the at least one flow cell.

7. The method of claim 5, wherein the at least one sensor is configured to detect the presence of one or more air bubbles within the flow cell.

8. The method of claim 5, further comprising at least one further sensor, wherein each sensor maintains communication with the reader during the performance of the at least one assay protocol such that the at least one sensor transmits data regarding the physical event or the electrochemical state.

9. The method of claim 5, wherein the reader controls the performance of the assay at least partially based on the information received from the at least one sensor regarding the physical event or the electrochemical state.

* * * * *